US009107713B2

(12) United States Patent
Horan et al.

(10) Patent No.: US 9,107,713 B2
(45) Date of Patent: Aug. 18, 2015

(54) PANCARPAL ARTHRODESIS BONE PLATE

(75) Inventors: Timothy J. Horan, West Chester, PA (US); Michael P. Kowaleski, Grafton, MA (US); Randy J. Boudrieau, Sherborn, MA (US); Alessandro Piras, Newry (GB); Brian Beale, Richmond, TX (US); Mark Ryan, Oregon, OH (US)

(73) Assignee: DePuy Synthes Products, Inc., Raynham, MA (US)

( * ) Notice: Subject to any disclaimer, the term of this patent is extended or adjusted under 35 U.S.C. 154(b) by 63 days.

(21) Appl. No.: 13/585,261

(22) Filed: Aug. 14, 2012

(65) Prior Publication Data

US 2013/0211459 A1    Aug. 15, 2013

Related U.S. Application Data

(60) Provisional application No. 61/531,243, filed on Sep. 6, 2011.

(51) Int. Cl.
*A61B 17/80* (2006.01)

(52) U.S. Cl.
CPC ......... *A61B 17/8061* (2013.01); *A61B 17/8052* (2013.01); *A61B 17/8057* (2013.01)

(58) Field of Classification Search
CPC ............... A61B 17/80; A61B 17/8052; A61B 17/8057; A61B 17/8061
USPC .................................. 606/280–299, 902–906
See application file for complete search history.

(56) References Cited

U.S. PATENT DOCUMENTS

| | | | | |
|---|---|---|---|---|
| 4,503,848 | A * | 3/1985 | Caspar et al. | 606/280 |
| 5,364,398 | A * | 11/1994 | Chapman et al. | 606/71 |
| 5,853,413 | A * | 12/1998 | Carter et al. | 606/281 |
| 6,221,073 | B1 * | 4/2001 | Weiss et al. | 606/60 |
| 6,406,478 | B1 * | 6/2002 | Kuo | 606/71 |
| 7,354,441 | B2 * | 4/2008 | Frigg | 606/261 |
| 7,695,472 | B2 * | 4/2010 | Young | 606/70 |
| 7,704,251 | B2 * | 4/2010 | Huebner et al. | 606/71 |
| 7,722,653 | B2 * | 5/2010 | Young et al. | 606/280 |
| 7,740,648 | B2 * | 6/2010 | Young et al. | 606/286 |
| 8,100,953 | B2 * | 1/2012 | White et al. | 606/280 |
| 8,147,530 | B2 * | 4/2012 | Strnad et al. | 606/290 |
| 8,177,818 | B2 * | 5/2012 | Wotton, III | 606/280 |
| 8,252,032 | B2 * | 8/2012 | White et al. | 606/280 |
| 8,394,130 | B2 * | 3/2013 | Orbay et al. | 606/280 |
| 8,419,775 | B2 * | 4/2013 | Orbay et al. | 606/281 |
| 8,808,334 | B2 * | 8/2014 | Strnad et al. | 606/286 |
| 8,814,918 | B2 * | 8/2014 | Orbay et al. | 606/286 |

(Continued)

FOREIGN PATENT DOCUMENTS

DE    20 2009 008 872 U1    9/2009

OTHER PUBLICATIONS

International Patent Application No. PCT/US2010/050738: International Search Report dated Jan. 2, 2013, 18 pages.

(Continued)

*Primary Examiner* — Michael T Schaper
*Assistant Examiner* — Amy Sipp
(74) *Attorney, Agent, or Firm* — Baker & Hostetler LLP

(57) ABSTRACT

A bone plate is configured for pancarpal arthrodesis. The bone plate can include a plurality of apertures that can be aligned with the metacarpal bones. The apertures can include a first portion and second portion that is longitudinally and laterally offset with respect to the first portion.

23 Claims, 9 Drawing Sheets

(56) References Cited

U.S. PATENT DOCUMENTS

| | | |
|---|---|---|
| 2005/0065524 A1* | 3/2005 | Orbay .............................. 606/69 |
| 2006/0200145 A1* | 9/2006 | Kay et al. ......................... 606/69 |
| 2006/0212035 A1* | 9/2006 | Wotton, III ...................... 606/69 |
| 2006/0229619 A1* | 10/2006 | Orbay et al. ..................... 606/69 |
| 2007/0173840 A1* | 7/2007 | Huebner ........................... 606/69 |
| 2007/0233114 A1* | 10/2007 | Bouman ........................... 606/69 |
| 2007/0239163 A1* | 10/2007 | Strnad et al. ..................... 606/72 |
| 2008/0045960 A1* | 2/2008 | Bruecker et al. ................. 606/69 |
| 2008/0051791 A1 | 2/2008 | Young et al. |
| 2008/0058815 A1* | 3/2008 | Young .............................. 606/69 |
| 2008/0125781 A1* | 5/2008 | Hoffman et al. ................. 606/69 |
| 2008/0140130 A1* | 6/2008 | Chan et al. ...................... 606/280 |
| 2008/0234749 A1* | 9/2008 | Forstein .......................... 606/291 |
| 2009/0171399 A1* | 7/2009 | White et al. ..................... 606/286 |
| 2009/0228010 A1 | 9/2009 | Gonzalez-Hernandez et al. |
| 2009/0281543 A1* | 11/2009 | Orbay et al. ..................... 606/70 |
| 2009/0318921 A1* | 12/2009 | White et al. ..................... 606/70 |
| 2010/0094351 A1* | 4/2010 | Haggenmaker et al. ........ 606/286 |
| 2010/0179599 A1* | 7/2010 | Derouet et al. ................. 606/280 |
| 2010/0312285 A1* | 12/2010 | White et al. ..................... 606/289 |
| 2012/0078312 A1* | 3/2012 | Federspiel et al. .............. 606/281 |
| 2012/0215223 A1* | 8/2012 | Chiodo et al. ................... 606/70 |
| 2012/0265253 A1* | 10/2012 | Conley et al. ................... 606/286 |
| 2012/0323284 A1* | 12/2012 | Baker et al. ..................... 606/289 |
| 2013/0178902 A1* | 7/2013 | Isch .................................. 606/246 |
| 2013/0190829 A1* | 7/2013 | Batsch et al. .................... 606/291 |
| 2013/0204307 A1* | 8/2013 | Castaneda et al. .............. 606/297 |

OTHER PUBLICATIONS

Anderson et al., "Surgical Case Report: Carpal Panarthrodesis," Dimensions in Surgery, DVM Pulse, Feb. 15-18, 2003.

* cited by examiner

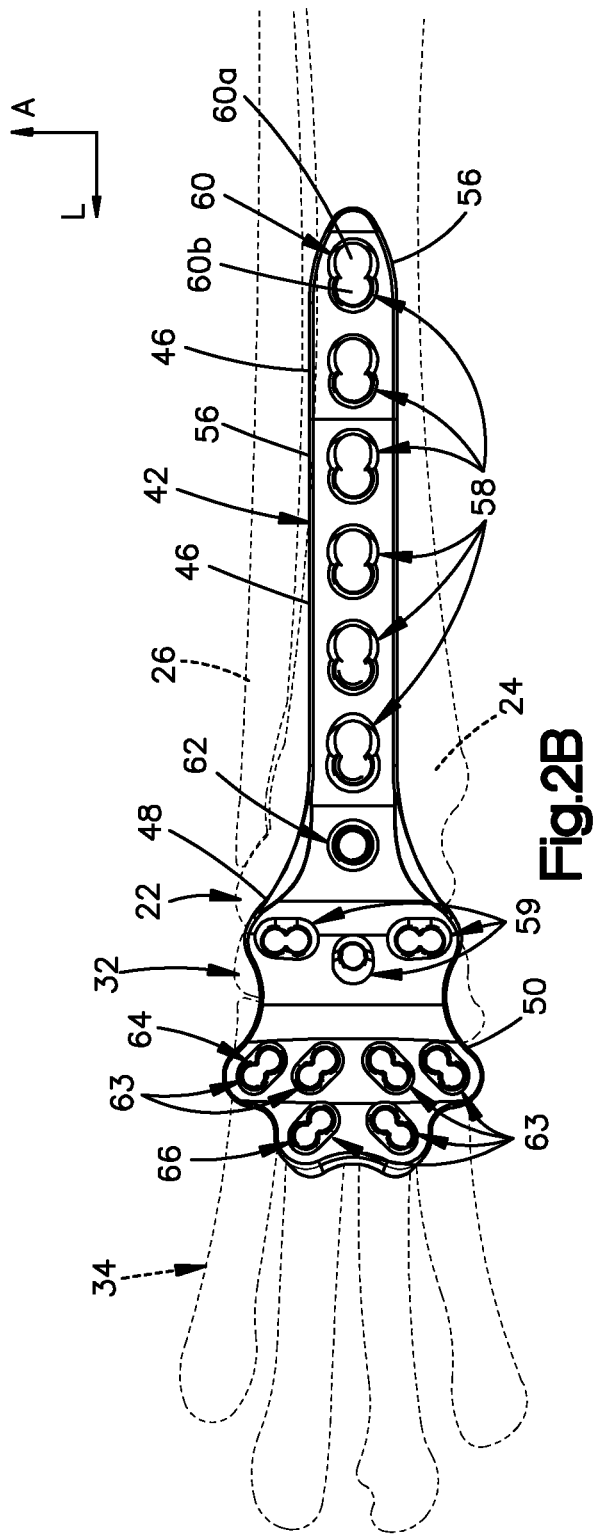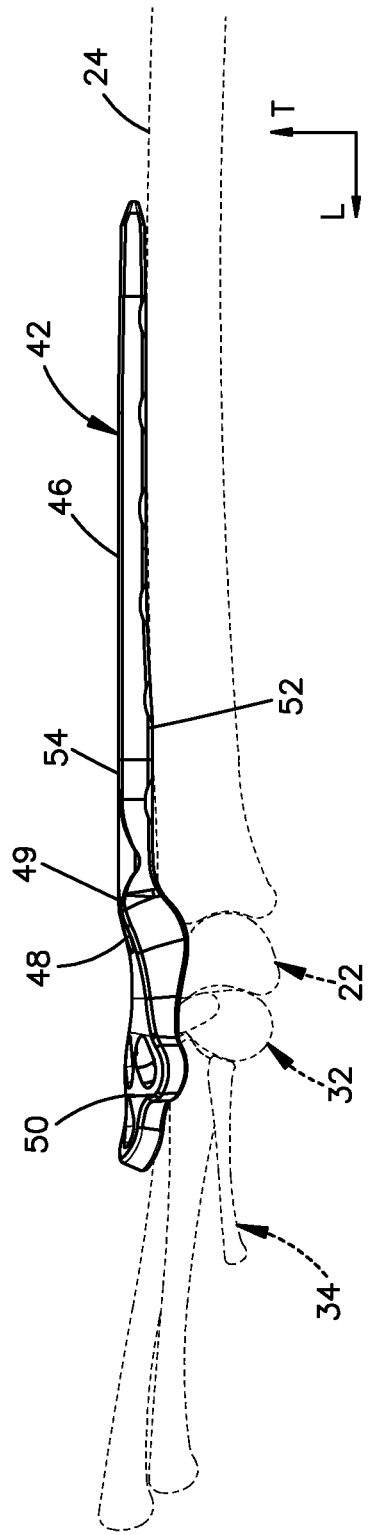

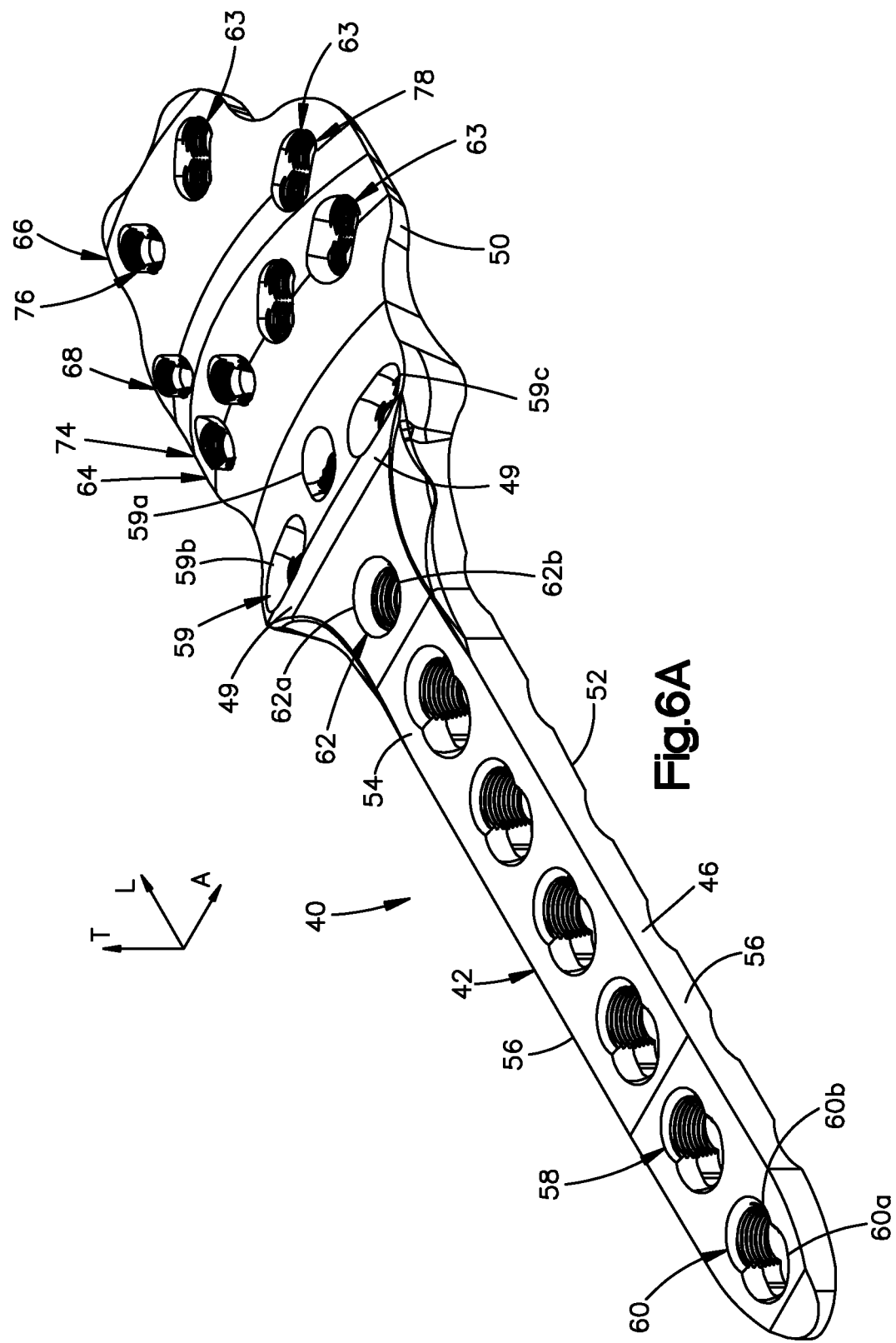

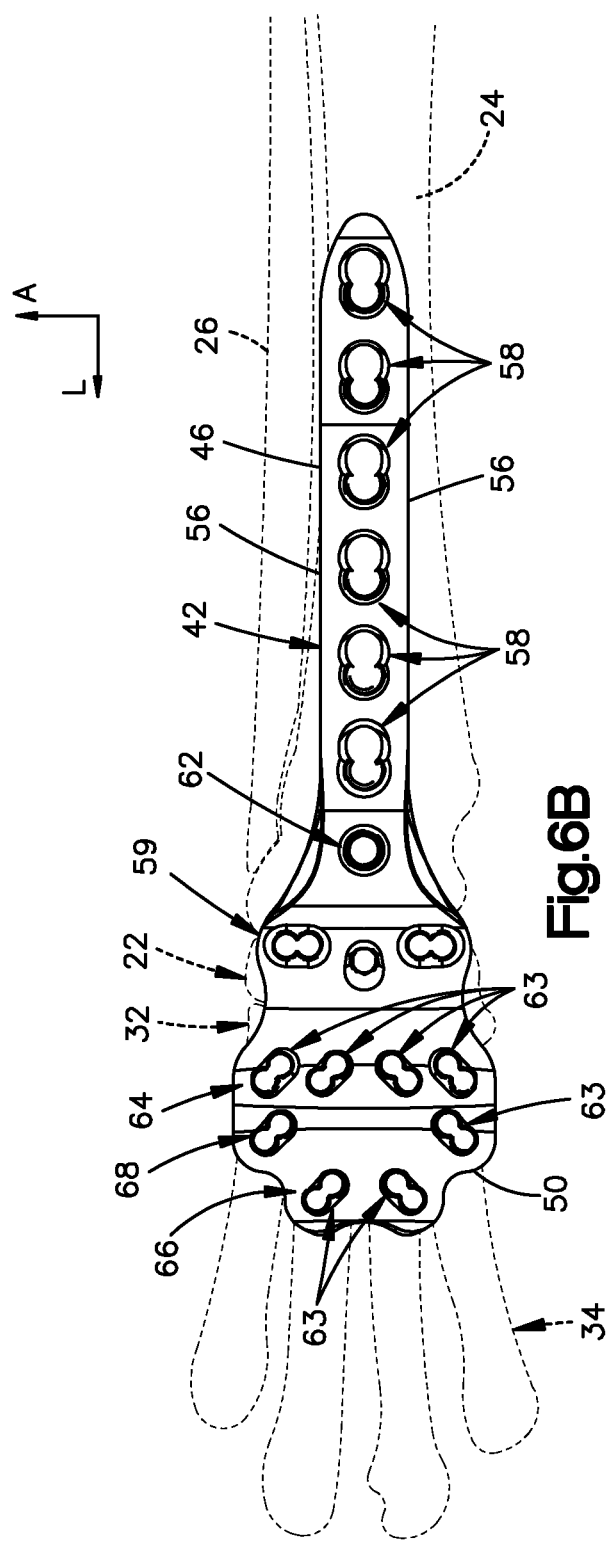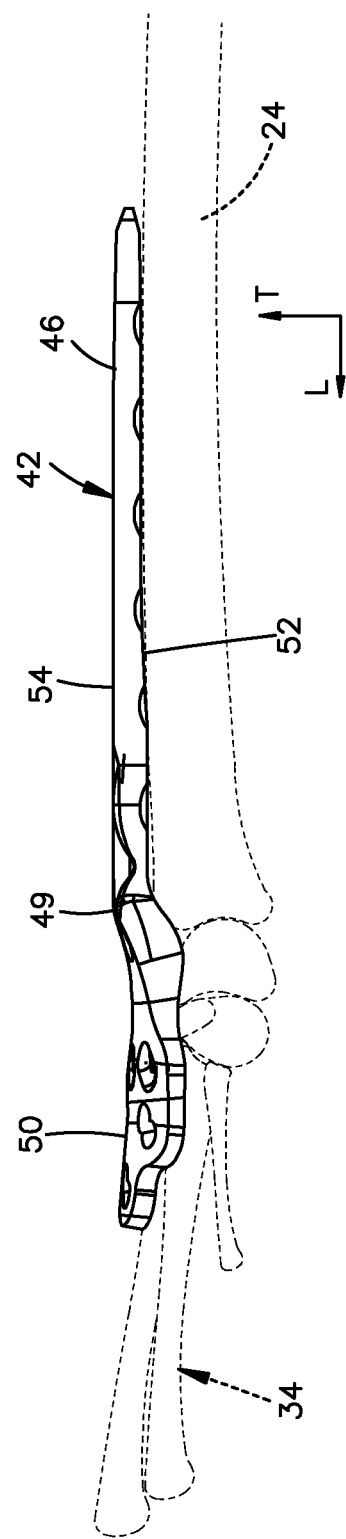

PANCARPAL ARTHRODESIS BONE PLATE

CROSS REFERENCE TO RELATED APPLICATIONS

This claims the benefit of U.S. Provisional Patent Application Ser. No. 61/531,243 filed on Sep. 6, 2011, the disclosure of which is hereby incorporated by reference as if set forth in its entirety herein.

BACKGROUND

Certain injuries of the carpus in quadrupeds, such as dogs, cats, horses, and the like, do not typically respond well to conservative treatment. For instance, when the carpus is hyperextended, the deep palmar carpal ligaments and the palmar carpal fibrocartilage do not typically heal naturally with enough strength to prevent future carpal hyperextension and associated pain.

As one example, referring to FIG. 1, the carpal region 20 of a canine includes a radius 24 and ulna 26, and carpal bones 21 that are disposed distal with respect to the radius 24 and the ulna 26. The carpal bones 21 include a plurality of proximal carpal bones 22 that are disposed distal with respect to the radius 24 and ulna 26 and include the radial carpal bone 28 and the ulnar carpal bone 30. The carpal bones 21 further include a plurality of distal carpal bones 32 that are distally spaced from the proximal carpal bones 22. The carpal region 20 further includes a plurality of metacarpal bones 34 that are distally spaced from the distal carpal bones 32. For instance, the carpal region 20 may include a first metacarpal bone 34a, a second metacarpal bone 34b, a third metacarpal bone 34c, a fourth metacarpal bone 34d, and a fifth metacarpal bone 34e. When arthrodesis is indicated in the carpal region, for instance due to trauma of the ligaments or fibrocartilage, a bone plate is typically fixed to the carpal region 20, including the radius 24, at least one of the carpal bones 22 and 32, and at least one of the metacarpal bones 34, such as a pair of metacarpal bones 34, so as to promote bone fusion. However, when certain conventional bone plates are placed over the respective bones of the carpal region 20, the screw holes of bone plates are in some instances insufficiently aligned to provide for adequate bone fixation.

SUMMARY

The present disclosure relates to methods and apparatus for pancarpal fixation. In accordance with one embodiment, an arthrodesis bone fixation plate is longitudinally elongate and includes a plurality of apertures. Some of the apertures are configured to be aligned with underlying metacarpal bones. Each of the apertures can include a first portion and a second portion that is open to the first portion, each configured to receive a bone screw. The second portion is offset with respect to the first portion in both the longitudinal direction and a lateral direction that is substantially perpendicular with respect to the longitudinal direction.

In an embodiment, an arthrodesis bone plate is configured to be attached to a carpal region of a patient and includes a bone plate body. The bone plate body is elongate along a longitudinal direction and defines a bone-facing inner surface and an opposed outer surface that is spaced from the inner surface along a transverse direction. Further, the bone plate body includes a proximal portion and a distal portion that is spaced from the proximal portion along the longitudinal direction that is substantially perpendicular to the transverse direction. The proximal portion is configured to be disposed over a radius of the carpal region. The distal portion is configured to be disposed over metacarpal bones of the carpal region. The bone plate body defines a plurality of apertures that extend from the outer surface to the inner surface at the distal region. A group of the plurality of apertures is spaced from one another along a lateral direction that is substantially perpendicular to the longitudinal and transverse directions, such that each aperture of the group is substantially aligned with at least a respective different one of at least four different metacarpal bones when the distal portion is disposed over the metacarpal bones and the proximal portion is disposed over the radius. Each of the apertures includes a first portion and a second portion that is open to the first portion. The first portion is offset with respect to the second portion. Further, each of the first and second portions of each aperture of the group configured to singly receive a bone anchor so as to attach the distal portion of the bone plate body to the respective four different metacarpal bones.

The first portion may be offset with respect to the second portion in both the longitudinal direction and the lateral direction. The plurality of apertures may be a plurality of distal apertures, and the bone plate may further include a plurality of proximal apertures that extend from the outer surface to the inner surface at the proximal region. Each proximal aperture is configured to receive a bone anchor so as to attach the proximal portion of the bone plate body to the radius. The proximal apertures may be spaced from one another along the longitudinal direction. The bone plate body may further include an intermediate portion that is disposed between and longitudinally spaced from the proximal and distal portions, and the intermediate portion is configured to be disposed over a radial carpal bone and an ulnar carpal bone of the carpal region when the proximal portion is disposed over the radius and the distal portion is disposed over the metacarpal bones. The bone plate may further include a plurality of intermediate apertures. Each of the intermediate apertures is configured to receive a bone anchor so as to attach the intermediate portion of the bone plate to the radial carpal bone and the ulnar carpal bone. The intermediate apertures may be spaced from each other along the lateral direction such that at least one intermediate aperture is aligned with the radial carpal bone and another intermediate aperture is aligned with the ulnar carpal bone when the bone plate body is disposed over the carpal region.

The bone plate body may include a first threaded surface that partially defines the first portion of at least one of the apertures, a second threaded surface that partially defines the second portion of at least one of the apertures, and a substantially flat surface that is disposed between the first and second threaded surfaces so as to separate the first portion from the second portion. The group of the plurality of apertures may be a first row that extends along the lateral direction. The group may be a first group, and the plurality of apertures includes a second group that is spaced from the first group along the longitudinal direction. At least two of the apertures may be configured to be aligned with the same metacarpal bone when the proximal portion is disposed over the radius and the distal portion is disposed over the metacarpal bones. The plurality of apertures may further include a third group of apertures that is spaced from the first and second groups along the longitudinal direction. The third group of apertures may be disposed between the first group and the second group of apertures.

The plurality of apertures may be configured to be positioned relative to one another such that two apertures are substantially aligned with at least a respective different one of at least four different metacarpal bones when the distal portion is disposed over the metacarpal bones and the proximal portion is disposed over the radius. The proximal portion may be offset with respect to the distal portion along the transverse direction. The proximal portion may be offset with respect to the intermediate portion along the transverse direction. The bone plate body may define a threaded surface and an unthreaded surface that cooperate to define at least one of the apertures, and the unthreaded surface is spaced from the threaded surface along the transverse direction.

In an embodiment, the bone plate includes a bone plate body that is elongate along a longitudinal direction and defines a bone-facing inner surface and an opposed outer surface that is spaced from the inner surface. Further, the bone plate body defines at least one aperture that extends from the outer surface to the inner surface. The aperture includes a first portion and a second portion that is spaced from the first portion along a first direction and open to the first portion. Each of the first portion and the second portion is configured and sized to individually receive a bone anchor so as to attach the bone plate body to an underlying bone. The bone plate body may further define a neck that is connected between the first and second portions. The neck defines at least one substantially flat surface that is substantially planar along the first direction.

Each of the of the first and second portions may define a respective maximum cross-sectional dimension along a second direction that is substantially perpendicular to the first direction. The neck may define a maximum cross-sectional dimension along the second direction, such that the maximum cross-sectional dimension of the neck is less than the maximum cross-sectional dimension of each of the first and second portion. The inner and outer surfaces of the bone plate body may be spaced along a transverse direction. The first and second directions may be angularly offset with respect to the transverse direction. The bone plate body may define first and second opposed sides that extend between the inner and outer surface. The first and second sides may be spaced from each other along a lateral direction that is substantially perpendicular to the transverse direction. The first direction may extend along the lateral direction.

The bone plate body may define first and second opposed sides that extend between the inner and outer surfaces, the first and second sides spaced from each other along a lateral direction that is substantially perpendicular to the transverse direction, and the first direction is angularly offset with respect to the lateral direction. The first and second portions may be symmetrical with respect to each other about the neck. The first portion may be concave with respect to the second portion, and the second portion may be concave with respect to the first portion. The first portion may be substantially arc-shaped and the second portion is substantially arc shaped. Each of the first and second portions defines an outer region that is substantially unthreaded, and an inner region that is threaded, the inner region disposed closer to the inner surface of the bone plate body than the outer region.

The present disclosure also relates to methods of bone fixation. In an embodiment, the method includes one or more of the following steps: (a) placing a bone plate onto a carpal region of a patient, the bone plate including a bone plate body that defines a proximal portion, a distal portion that is spaced from the proximal portion along a longitudinal direction, a plurality of apertures extending through the distal portion, each of the apertures including a first portion and a second portion that is spaced from the first portion and open to the first portion, each of the first and second portions configured and sized to individually receive a bone anchor; (b) positioning the bone plate body on the carpal region such that the proximal portion overlays at least a portion of a radius of the carpal region and the distal portion overlays at least four metacarpal bones; (c) identifying a select one of the first and second portions of at least one of the apertures to receive a bone anchor; and (d) inserting the bone anchor through the identified select one of the first and second portions of the at least one of the apertures so as to attach the distal portion to at least one of the metacarpal bones. The placing step may include aligning at least one of the apertures with each of the four metacarpal bones. The placing step may include aligning at least two of the apertures with each of the four metacarpal bones. The apertures may be distal apertures, and the bone plate may further define proximal apertures at the proximal region. The bone screw may be a distal bone screw, and the method may further include inserting a proximal bone screw through at least one of the proximal apertures and into the radius so as to couple to bone plate to the radius.

BRIEF DESCRIPTION OF THE DRAWINGS

The foregoing summary, as well as the following detailed description of an example embodiment of the application, will be better understood when read in conjunction with the appended drawings, in which there is shown in the drawings an example embodiment for the purposes of illustration. It should be understood, however, that the application is not limited to the precise arrangements and instrumentalities shown. In the drawings:

FIG. 2B is a top plan view of the pancarpal arthrodesis bone plate illustrated in FIG. 2A, shown placed over a carpus to be fixed;

FIG. 2C is side elevation view of the pancarpal arthrodesis bone plate illustrated in FIG. 2B;

FIG. 6A is a perspective view of a pancarpal arthrodesis bone plate constructed in accordance with one embodiment;

FIG. 6B is a top plan view of the pancarpal arthrodesis bone plate illustrated in FIG. 6A, shown placed over a carpus to be fixed; and FIG. 6C is a side elevation view of the pancarpal arthrodesis bone plate illustrated in FIG. 6B.

DETAILED DESCRIPTION

Figure 1:
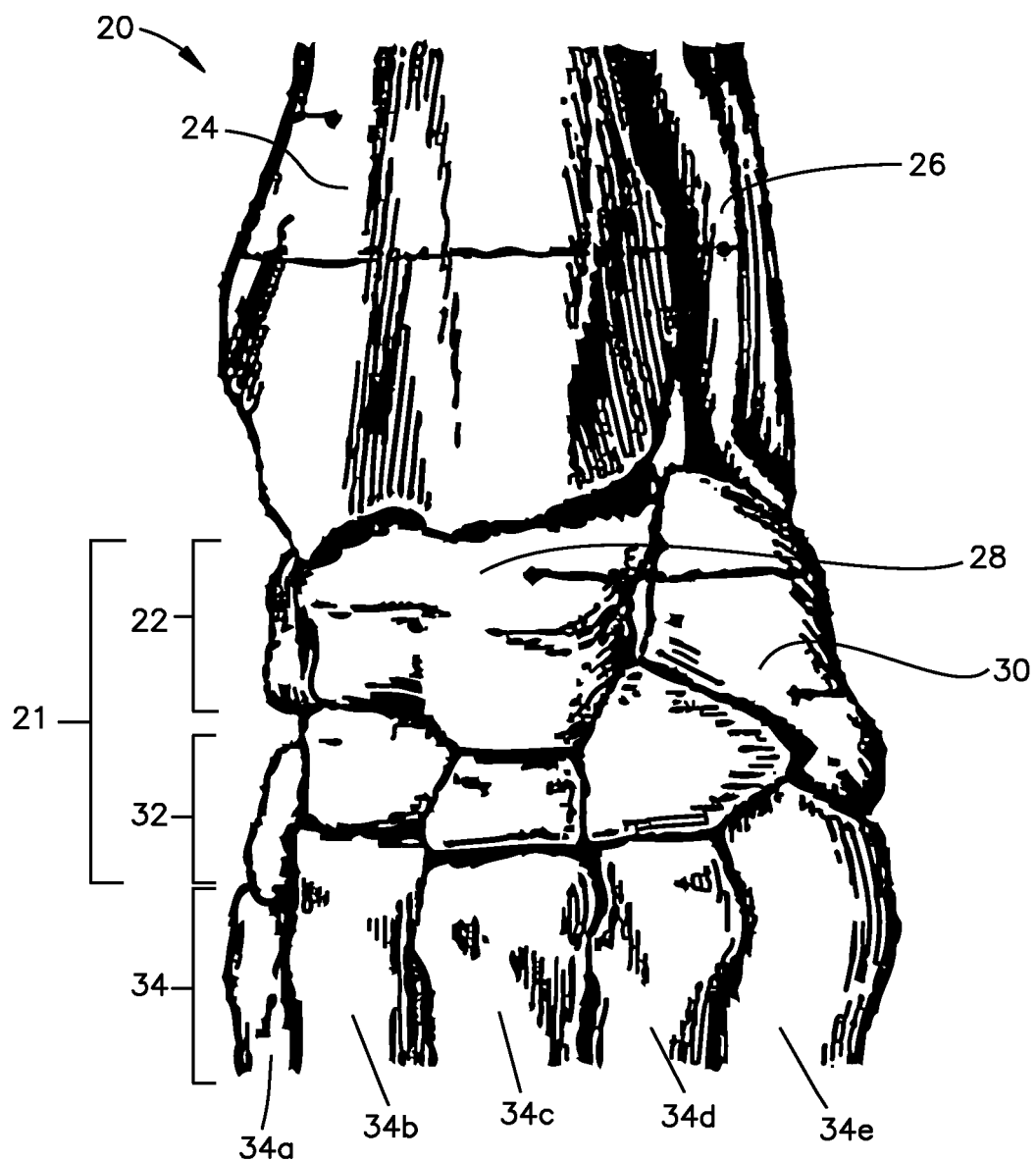
FIG. 1 is a top view of a left carpus of a canine.
Figure 2A:
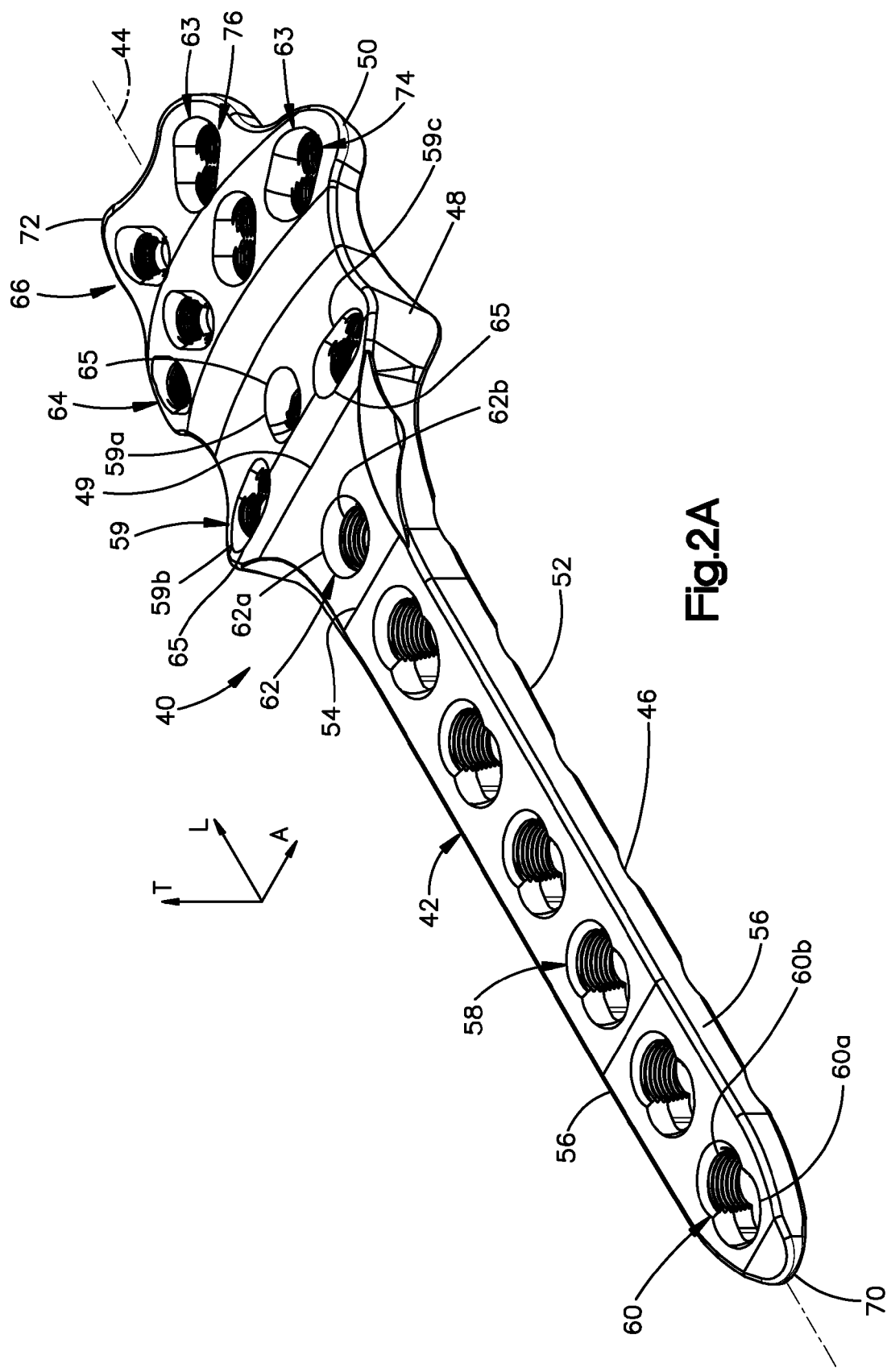
FIG. 2A is a perspective view of a pancarpal arthrodesis bone plate constructed in accordance with one embodiment.
Figure 2D:
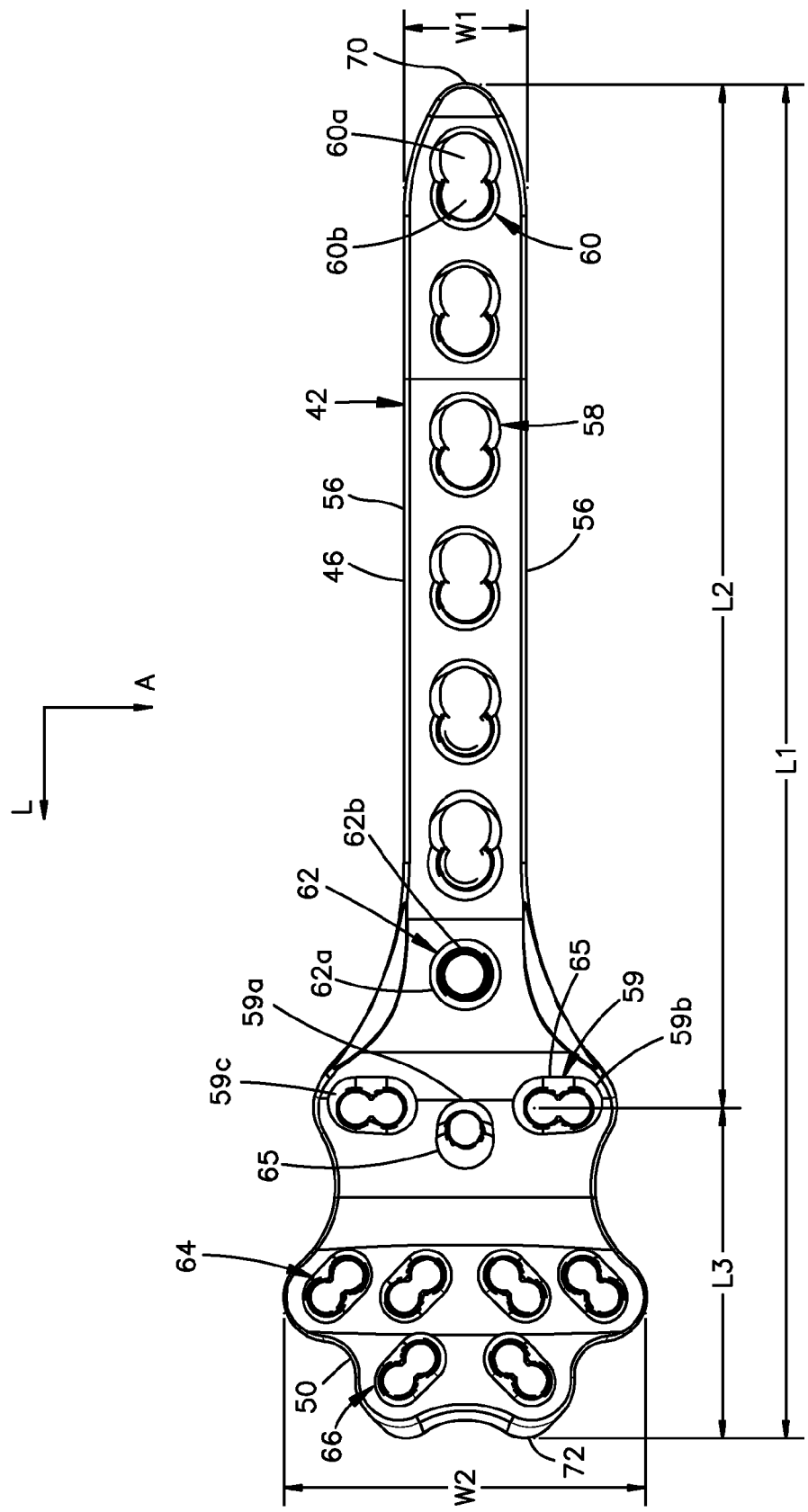
FIG. 2D is a top plan view of the pancarpal arthrodesis bone plate illustrated in FIG. 2B, including dimensions (mm) in accordance with one embodiment, it being appreciated that the dimensions can differ in any manner as desired consistent with a pancarpal arthrodesis bone plate.
Figure 3:
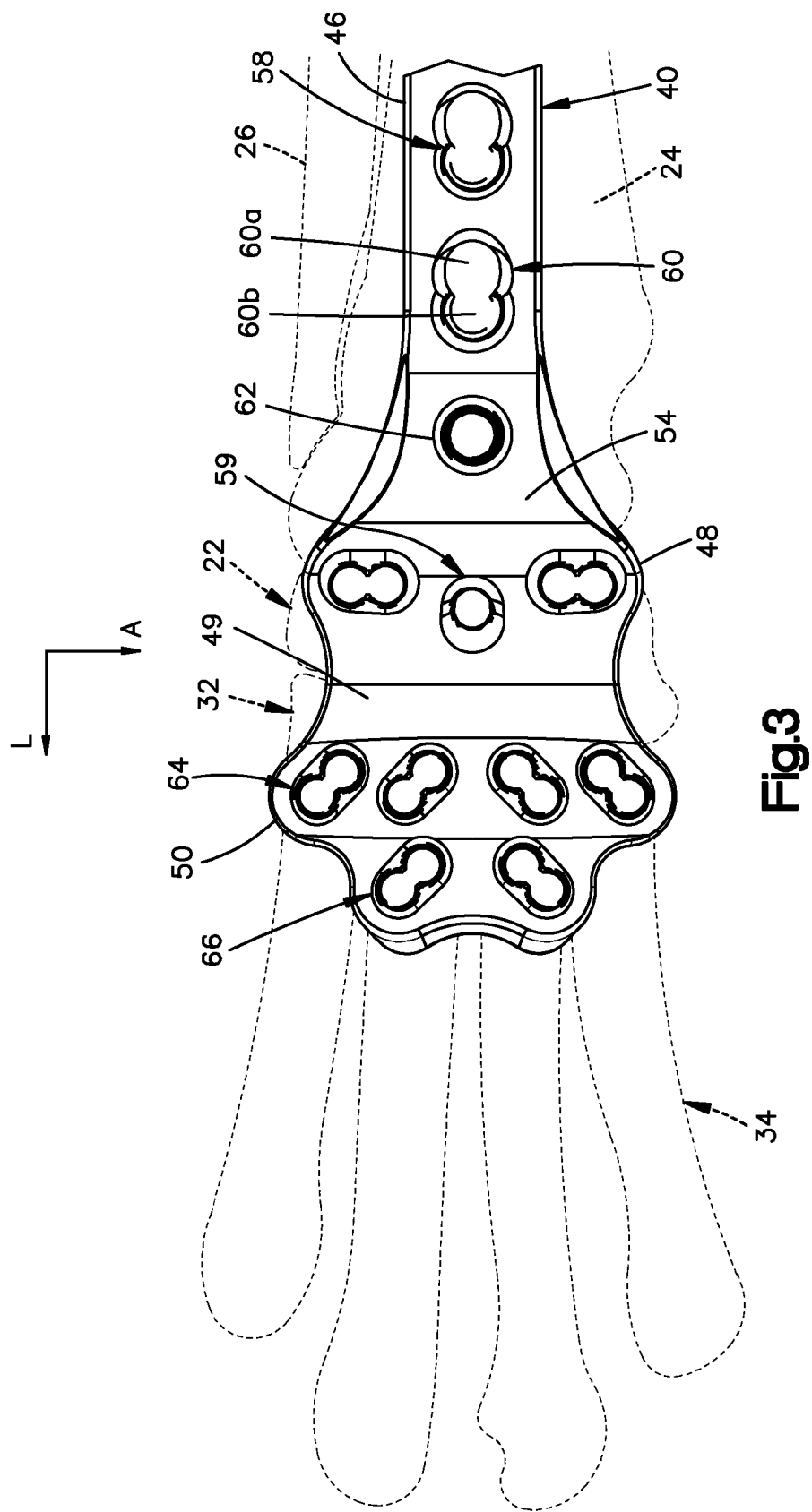
FIG. 3 is a top plan view of a portion of the pancarpal arthrodesis bone plate illustrated in FIG. 2B.

Referring to FIGS. 2A-3, a pancarpal arthrodesis bone plate 40 can be geometrically configured for fixation to an underlying bone, such as the bones of the carpal region 20 of a quadruped, so as to fix the radius 24, ulna 26, proximal carpal bones 22, distal carpal bones 32, and metacarpal bones 34 with respect to one another. The pancarpal arthrodesis bone plate 40 is elongate along a longitudinal direction L, defines a width along a lateral direction A that is perpendicular or substantially perpendicular to the longitudinal direction L, and a thickness along a transverse direction T that is perpendicular or substantially perpendicular to both the longitudinal direction L and the lateral direction A. In this regard, it should be appreciated that the various directions can extend along directions that are 90° angularly offset from each other, or anywhere within the range of approximately 45° and approximately 90° angularly offset from each other.

The pancarpal arthrodesis bone plate 40 includes a plate body 42 that extends substantially along a central longitudinal axis 44 that is oriented along a proximal-distal direction when aligned for fixation to the underlying carpal region 20 in the manner described herein. The pancarpal arthrodesis bone plate 40 includes a proximal portion 46 that is configured to be placed over and subsequently fixed to the radius 24, an intermediate portion 48 that is disposed distally from the proximal portion 46 and configured to be placed over and subsequently fixed to at least one or both of the proximal carpal bones 22, and a distal portion 50 that is spaced distally from the intermediate portion 48 and configured to be placed over and subsequently fixed to at least one or more, such as four, of the metacarpal bones 34, including the second, third, fourth, and fifth metacarpal bones 34b, 34c, 34d, and 34e. Accordingly, the intermediate portion 48 is disposed between the proximal portion 46 and the distal portion 50 along the longitudinal axis 44. In other words, the proximal portion 46, distal portion 50, and the intermediate portion 48 are spaced from one another along the longitudinal direction L. The intermediate portion 48 is disposed between and longitudinally spaced from the proximal portion 46 and the distal portion 50. In use, the intermediate portion 48 is configured to be disposed over the radial carpal bone 28 and the ulnar carpal bone 30 when the proximal portion 46 is disposed over the radius 24 and the distal portion 50 is disposed over the metacarpal bones 34.

The plate body 42 further define a bone-facing inner surface 52 that is configured to face the underlying bone, and an opposed outer surface 54 that is spaced from the inner surface 52 along the transverse direction T. The plate body 42 further defines opposed side surfaces 56 that are spaced from each other along the lateral direction A. The inner surface 52 can be configured and sized to fit over an underlying bone such as the carpal region 20 of a canine. For instance, the inner surface 52 can be curved along the lateral direction A between the side surfaces 56 so as to generally conform to the underlying radius 24. Furthermore, the inner surface 52 can extend substantially longitudinally along the proximal portion 46, and can be curved transversely inwardly along the longitudinal direction L from the proximal portion 46 to the intermediate portion 48. For instance, the inner surface 52 can be disposed transversely inwardly at the intermediate portion 48 (at a location aligned with the underlying proximal carpal bones 22) with respect to the proximal portion 46 and the distal portion 50. The inner surface 52 can abut the proximal carpal bones 22 or can be slightly spaced from the proximal carpal bones 22 as desired. The inner surface 52 can curve transversely outward from the intermediate portion 48 to the distal portion 50 so as to generally conform to the underlying metacarpal bones 34. The side surfaces 56 can be laterally spaced apart a distance at the proximal portion 46 that is less than both the intermediate portion 48 and the distal portion 50. The side surfaces 56 can be laterally spaced apart a distance at the intermediate portion 48 that is less than at the distal portion 50. The side surfaces 56 can neck inwardly between the intermediate portion 48 and the distal portion 50. The side surfaces 56 may also be referred as sides.

The plate body 42 may further include a bent portion 49 that interconnects the proximal portion 46 and the intermediate portion 48. The bent portion 49 separates the proximal portion 46 from the intermediate portion 48 such that the proximal portion 46 is spaced from the intermediate portion 48 along the transverse direction T. In other words, the proximal portion 46 is offset with respect to the distal portion 50 along the transverse direction T. Further, the proximal portion 46 is offset with respect to the intermediate portion 48 along the transverse direction T. Accordingly, when the plate body 42 is disposed over the carpal region 20, the proximal portion 46 can be placed over the radius 24, while the intermediate portion 48 is placed over the proximal carpal bones 22 and the distal portion 50 is placed over the metacarpal bones 34. Thus, the proximal portion 46 is configured to be disposed over the radius 24, and the distal portion 50 is configured to be disposed over the metacarpal bones 34.

The pancarpal arthrodesis bone plate 40 can define a plurality of apertures configured to receive a bone anchor so as to fix the plate body 42 to the underlying bone. The apertures extend from the outer surface 54 to the inner surface 52 along the transverse direction T. For instance, the pancarpal arthrodesis bone plate 40 can define a first plurality of proximal apertures 58 that extend transversely through the proximal portion 46 of the plate body 42, a second plurality of intermediate apertures 59 that extend transversely through the intermediate portion 48 of the plate body 42, and a third plurality of distal apertures 63 that extend transversely through the distal portion 50 of the plate body 42.

Each of the first plurality of proximal apertures 58 can be spaced longitudinally, can be longitudinally aligned along the central axis 44 as desired, and can be configured as desired so as to receive a bone anchor, such as a bone screw, so as to fix the proximal portion 46 to the underlying radius 24. Each of the proximal apertures 58 can extend from the outer surface 54 to the inner surface 52 at the proximal region 46. The proximal apertures 58 may be spaced from one another along the longitudinal direction L. At least one up to all of the proximal apertures 58 can be configured as combination apertures 60 having a first or proximal portion 60a and a second or distal portion 60b that is open to the proximal portion 60a. Thus, each of the proximal portion 60a and the distal portion 60b can be open to each other so as to define an enclosed aperture 60. In other words, the proximal portion 60a and the distal portion 60b are in communication with each other such that the proximal portion 60a and the distal portion 60b collectively define an enclosed aperture 60. The proximal portion 60b of an aperture 60 can be spaced from the distal portion 60b of that same aperture 60 along the longitudinal direction. In accordance with the illustrated embodiment, either or both of the proximal and distal portions 60a and 60b can be unthreaded and longitudinally elongate so as to receive a compression screw that is driven into the underlying radius 24. The aperture 60 can be referred to as a combination hole (or combi-hole) as understood by those having ordinary skill in the art. The plate body 42 can translate with respect to the compression screw prior to tightening the compression screw against the plate body 42, thereby compressing the plate body 42 against the underlying bone. Furthermore, either or both of the proximal and distal portions 60b can be threaded so as to mate with a threaded head of a locking screw. Furthermore, the distal portion 60b can define a variable angle hole portion that can mate with the threaded head of the locking screw when the locking screw is oriented at a non-zero angle with respect to the transverse direction T.

Furthermore, at least one up to all of the proximal apertures 58 can define a stacked combination hole 62. For instance, the stacked combination hole 62 can define a transverse outer unthreaded surface 62a and an inner transverse threaded surface 62b disposed transversely inwardly with respect to the unthreaded surface. Accordingly, a compression screw can be inserted through the stacked combination hole 62 and driven into the underlying bone such that the unthreaded head abuts the transverse outer unthreaded surface 62a. Alternatively, a locking screw can be inserted through the stacked combination hole 62 and driven into the underlying bone such that the threaded head mates with the inner transverse threaded surface 62b. Thus, each of the proximal apertures 58 can be configured to selectively receive either a compression screw or a locking screw. In accordance with the illustrated embodiment, the proximal apertures 58 include six combination apertures 60 and a stacked combination hole 62 that is spaced distally from the combination apertures 60, though it should be appreciated that the proximal apertures 58 can include as many combination apertures 60 and stacked combination holes 62 as desired. Alternatively, at least one up to all of the proximal apertures 58 can be configured as any suitably constructed aperture configured to fix the plate body 42 to the underlying bone as desired.

The intermediate apertures 59 can likewise be configured as desired so as to receive a suitable bone anchor, such as a bone screw, so as to fix the plate body 42 to the underlying bone, which can be one of the proximal carpal bones 22. For instance, the intermediate apertures 59 may be spaced from one another along the lateral direction A such that at least one aperture is aligned with the radial carpal bone 28 and another intermediate aperture 59 is aligned with the ulnar carpal bone 30 when the bone plate body 42 is disposed over the carpal region 20. At least one or more up to all of the intermediate apertures 59 can be threaded so as to mate with the threaded head of a locking screw that is inserted through the aperture into the underlying bone. Alternatively or additionally, at least one or more up to all of the intermediate apertures 59 can be unthreaded so as to receive a compression screw that is inserted through the aperture into the underlying bone so that the head of the compression screw abuts the plate body 42 so as to compress the plate body 42 against the underlying bone. Alternatively or additionally still, at least one or more up to all of the intermediate apertures 59 can be configured as a stacked combination hole of the type described above. Each of the intermediate apertures 59 is configured to receive a bone anchor so as to attach the intermediate portion 48 to the radial carpal bone 28 and the ulnar carpal bone 30.

The intermediate apertures 59 can include a central intermediate aperture 59a that is aligned with the proximal apertures 58 along the longitudinal axis 44, and first and second outer pairs of intermediate apertures 59b and 59c that are laterally outwardly spaced on opposed sides of the central intermediate aperture 59a. The central intermediate aperture 59a can also be spaced distally with respect to the pairs of apertures 59b and 59c. Each aperture of the pairs of the intermediate apertures 59b and 59c can be spaced laterally apart a distance that is less than the distance that the central aperture 59a is spaced from the laterally inner apertures of the pairs of apertures 59b and 59c. The central aperture 59a and the first pair of apertures 59b can be aligned with the radial carpal bone 28 and the second pair of apertures 59c can be aligned with the ulnar carpal bone 30. Each of the apertures of the pairs of apertures 59b and 59c can be separate enclosed laterally spaced apertures, or can alternatively be open to each other so as to define a combination aperture, whereby the apertures of each of the pairs of apertures 59b and 59c are laterally open to each other. Further, each of the apertures 59a-59c can define a recessed region 65 that extend transversely into the outer surface 54 and can be shaped substantially as an oval, circle or otherwise shaped as desired. The recessed regions 65 can be unthreaded, and the apertures 59a-59c can be threaded or unthreaded. Thus, the apertures 59a-59c can define stacked combination holes. Accordingly, a compression screw can be inserted through the apertures 59a-59c and driven into the underlying bone such that the unthreaded head abuts a transverse outer unthreaded surface. Alternatively, a locking screw can be inserted through the apertures 59a-59c and driven into the underlying bone such that the threaded head mates with the inner transverse threaded surface. Thus, each of the apertures 59a-59c can be configured to selectively receive both a compression screw and a locking screw. Each recess 65 can also be configured so that a bone anchor can be inserted into an aperture (59a, 59b or 59c) and into the underlying bone at an oblique angle relative to the transverse direction T or the longitudinal axis 44. Each of the intermediate apertures 59 is configured to receive a bone anchor so as to attach the intermediate portion 48 to the radial carpal bone 28 and the ulnar carpal bone 30. The intermediate apertures 59 may be spaced from each other along the lateral direction A such that at least one intermediate aperture 59 is aligned with the radial carpal bone 28 and another intermediate aperture 59 is aligned with the ulnar carpal bone 30 when the bone plate body 42 is disposed over the carpal region 20.

The distal apertures 63 can be arranged in different groups such as the first group 74 and a second group 76. The first group 74 may include distal apertures 63 that are spaced from one another along the lateral direction A. Similarly, the second group 76 may include distal apertures 63 that are spaced from one another along the lateral direction A. The first group 74 of apertures 63 may be spaced from the second group 76 of apertures 63 along the longitudinal direction L. Each of the apertures 63 of the first group 74 is configured to be substantially aligned with at least a respective different one of at least two different metacarpal bones 34 when the distal portion 50 is disposed over the metacarpal bones 34 and the proximal portion 46 is disposed over the radius 24. For example, each of the apertures 63 of the first group 74 is configured to be substantially aligned with at least a respective different one of at least four different metacarpal bones 34 when the distal portion 50 is disposed over the metacarpal bones 34 and the proximal portion 46 is disposed over the radius 24. The first group 74 may be a first row 63, whereas the second group 76 may be a second row 66. Thus, the distal apertures 63 can be arranged in the first row 64 and the second row 66. While the first row 64 includes more apertures 63 than the second row 66, it should be appreciated that the rows 64 and 66 can include as many apertures 63 as desired. For instance, each of the distal apertures 63 of the first row 64 can be positioned so as to be aligned with a different metacarpal bone 34. Likewise, each of the distal apertures 63 of the second row 66 can be positioned so as to be aligned with a different metacarpal bone 34. In accordance with the illustrated embodiment, the first row 64 includes four apertures 63 that are configured to be aligned with the second, third, fourth, and fifth metacarpal bones 34 when the pancarpal arthrodesis bone plate 40 is placed over the carpal bones 21 so as to be fixed to the carpal region 20. The ability to fix the arthrodesis bone plate 40 to more than two metacarpals can better distribute loads and thus achieve better stress distribution compared to certain conventional pancarpal bone plates that are configured to secure to one or two metacarpal bones. In accordance with the illustrated embodiment, the second row 66 includes two apertures 63 that are configured to be aligned with the third and fourth metacarpal bones 34 when the pancarpal arthrodesis bone plate 40 is placed over the carpal bones 21 so as to be fixed to the carpal region 20. It should be appreciated that the first and second rows 64 and 66 can include any number of apertures 63 aligned with any of the metacarpal bones 34 as desired.

Figure 4A:
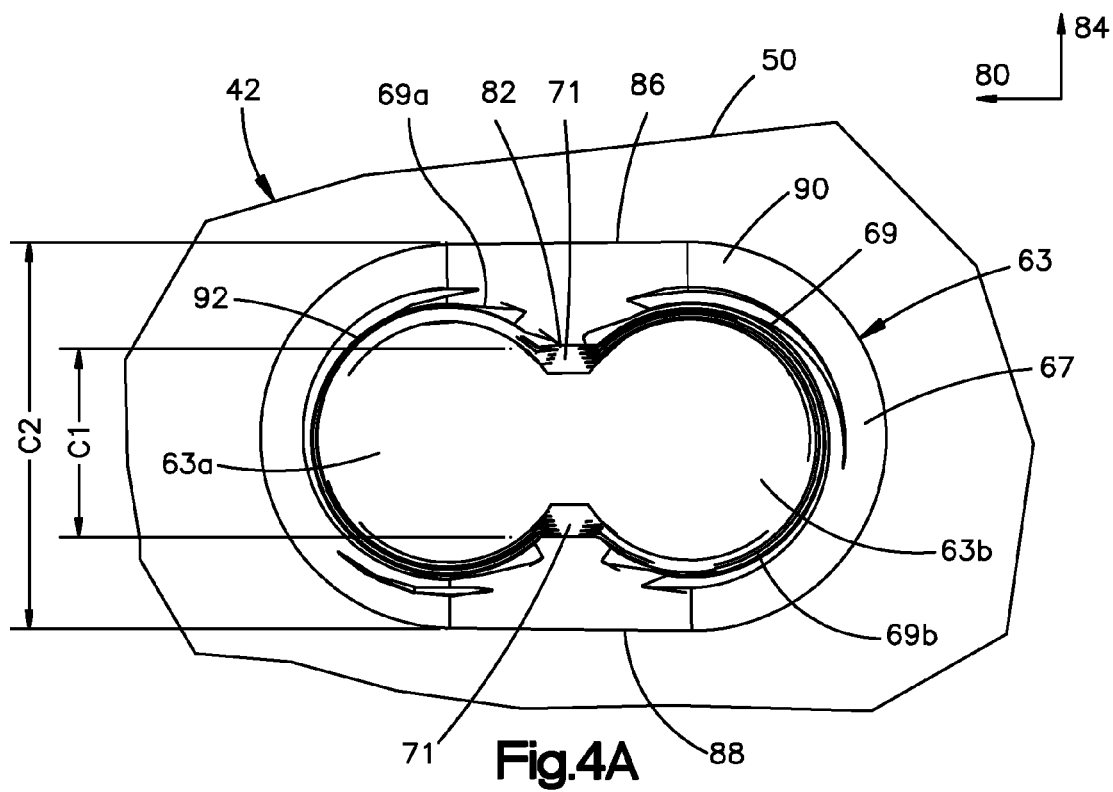
FIG. 4A is an enlarged top plan view of a distal portion of the pancarpal arthrodesis bone plate illustrated in FIG. 3, showing a distal aperture
Figure 4B:
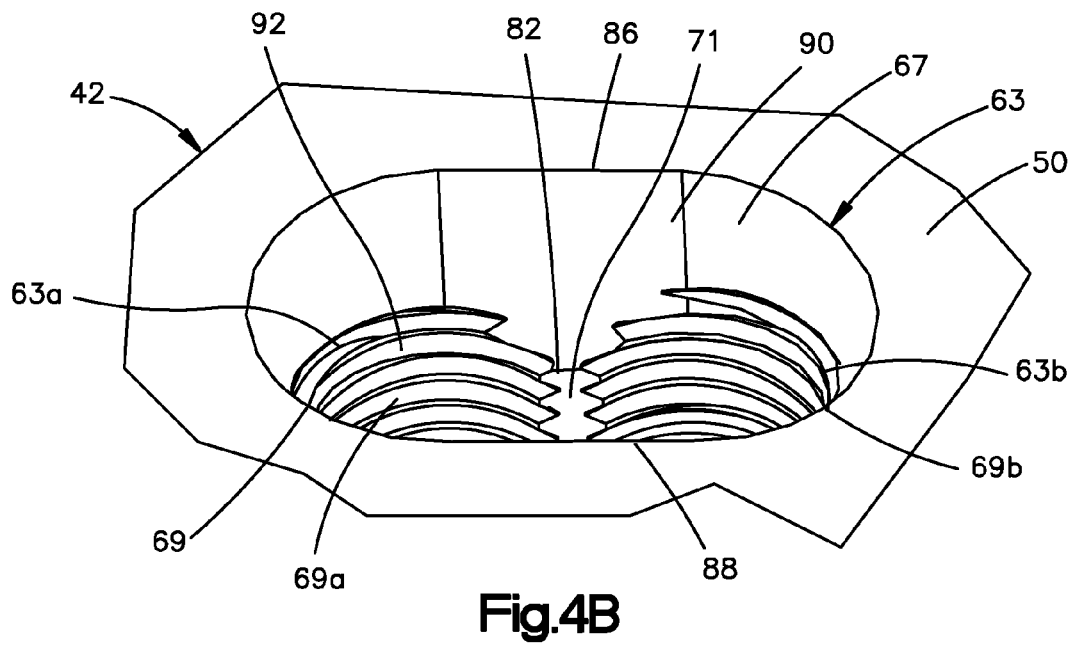
FIG. 4B is an enlarged perspective view of the distal portion of the pancarpal arthrodesis bone plate illustrated in FIG. 4A, showing the distal aperture.

Referring also to FIGS. 4A-B, at least one up to all of the distal apertures 63 can include a first portion 63a and a second portion 63b that is spaced from the first portion 63a, such that the first and second portions 63a and 63b are open to each other. In other words, the first portion 63a and the second portion 63b of a distal aperture 63 can be in communication with each other. Each of the first portion 63a and the second portion 63b is configured to singly receive a bone anchor such as a bone screw so as to attach the distal portion 50 to the metacarpal bones 34. In words, each of the first portion 63a and the second portion 63b is configured to individually receive a bone anchor. The first and second portions 63a and 63b can be substantially equally sized, or sized differently as desired. The second portion 63b is both longitudinally and laterally offset with respect to the first portion 63a. In accordance with the illustrated embodiment, the second portion 63b is disposed distally and laterally outward (e.g., spaced further from the central axis 44 and closer to the respective side surface 56) with respect to the first portion 63a. For instance, the second portion 63b and the first portion 63a can be spaced from each other along a direction that defines an angle with respect to the central axis 44. The angle can be anywhere between 0 and 90 degrees, such as between 20 and 70 degrees, more particularly between 35 and 55 degrees, such as approximately 45 degrees. In an embodiment, the first portion 63a may be offset with respect to the second portion 63b in both the longitudinal direction L and the lateral direction A. The first portion 63a may be concave with respect to the second portion 63b, and the second portion 63b may be concave with respect to the first portion 63a.

At least one or both of the first and second portions 63a and 63b can be configured as desired so as to receive a suitable bone anchor, such as a screw, so as to fix the plate body 42 to the underlying bone, which can be one of the metacarpal bones 34. For instance, at least one or more up to all of the first and second portions 63a and 63b can be threaded so as to mate with the threaded head of a locking screw that is inserted through the respective portion aperture into the underlying bone. Alternatively or additionally, at least one or more up to all of the first and second portions 63a and 63b can be unthreaded so as to receive a compression screw that is inserted through the aperture into the underlying bone so that the head of the compression screw abuts the plate body 42 so as to compress the plate body 42 against the underlying bone. Alternatively or additionally still, at least one or more up to all of the first and second portions 63a and 63b can be configured as a stacked combination hole of the type described above. For instance, one or more distal apertures 63 can be defined by a threaded surface 69 of the plate body 42 and a transverse outer unthreaded surface 67 that is disposed transversely outward with respect to the threaded surface 69. The unthreaded surface 67 may be spaced from the threaded surface 63 along the transverse direction T. Accordingly, a compression screw can be inserted through the aperture 63 and driven into the underlying bone such that the unthreaded head abuts the transverse outer unthreaded surface 67. Alternatively, a locking screw can be inserted through the aperture 63 and driven into the underlying bone such that the threaded head mates with the inner transverse threaded surface 69 of one of the portions 63a and 63b. Thus, each of the distal apertures 63 can be configured to selectively receive either a compression screw or a locking screw. The first portion 63a may be partially defined by a first inner arc-shaped threaded surface 69a, and the second portion 63b may be partially defined by a second inner arc-shaped threaded surface 69b. Each of the first portion 63a and the second portion 63b may define an outer region 90 that is substantially unthreaded, and an inner region 92 that is threaded. The inner region 92 may be disposed closer to the inner surface 52 of the bone plate body 42 than the outer region 90.

The bone plate body 42 may define a neck 82 that is connected between the first portion 63a and the second portion 63b of at least one of the distal apertures 63. As discussed above, each of the first portion 63a and the second portion 63b is configured to individually receive a bone anchor. The neck 82 defines at least one substantially flat unthreaded surface 71 that is substantially planar along a first direction 80. The first direction 80 may be oblique, parallel, or perpendicular to the longitudinal direction L. In the depicted embodiment, the neck 82 includes two substantially flat surfaces 71 that are spaced from each other along a second direction 84. The second direction 84 may be substantially perpendicular to the first direction 80. It is envisioned that the second direction 84 may be oblique, parallel, or perpendicular to the longitudinal direction L. The substantially flat surfaces 71 may be elongate along the transverse direction T. The substantially flat surfaces 71 separate the threaded surface 69a that partially defines the first portion 63a from the threaded surface 69 that partially defines the second portion 63b along the first direction 80. The first portion 63a can therefore be spaced from the second portion 63b along the first direction 80. For instance, one aperture 63 may include two opposed substantially flat surfaces 71 that are spaced from one another both the longitudinal direction L and a lateral direction A. The substantially flat surfaces 71 are disposed the between the first portion 63a and the second portion 63b so as to avoid sharp edges between the first portion 63a and 63b, thereby minimizing the occurrences of burrs or debris when screwing a bone anchor through the aperture 63. In the depicted embodiment, one or more of the apertures of the bone plate 40, such as the distal apertures 63, is a double threaded aperture. The first threaded surface 69a can also be referred to as first threads, and the second threaded surface 69b can also be referred to as second threads. Thus, the bone plate body 42 includes first threads 69a that are disposed around the first portion 63a and second threads 69b that are disposed around the second portion 63b. The first threads 69a are spaced from the second threads 69b by the neck 82 such that the first threads 69a do not overlap the second threads 69b.

The neck 82 may define a maximum cross-sectional dimension C1 that is substantially perpendicular to the first direction 80. In the depicted embodiment, the maximum cross-sectional dimension C1 may extend from one substantially flat surface 71 to the other substantially flat surface 71 along the second direction 84. No other dimension that extends from one substantially flat surface 71 to the other substantially flat surface 71 along the second direction 84 is greater than the maximum cross-sectional dimension C1. Each distal aperture 63 may define a maximum cross-sectional dimension C2 that extends from a first end 86 to a second end 88 along the second direction 84. No other dimension that extends from the first end 86 to the second end 88 along the second direction 84 is greater than the maximum cross-sectional dimension C2. The maximum cross-sectional dimension C2 of the distal aperture 63 may also be the maximum cross-sectional dimension of each of the first portion 63a and the second portion 63. However, the first portion 63a and the second portion 63b may have different maximum cross-sectional dimensions. In the depicted embodiment, the cross-sectional dimension C1 of the neck 82 is less than the maximum cross-sectional dimension C2 of the each of the first portion 63a and the second portion 63b. The first portion 63a and the second portion 63b may be symmetrical with respect to each other about the neck 82.

During operation, bone screws can be inserted into at least a select one or more up to all of the distal apertures 63 so as to fix the distal portion 50 to the underlying metacarpals 34. For instance, a bone screw can be driven through those of the distal apertures 63 that are sufficiently aligned with the underlying metacarpal bone 34. For instance, a bone screw can be selectively inserted into one of the first and/or second portions 63a and 63b of a given distal aperture 63, depending on, for instance, which of the portions 63a and 63b is better aligned with the underlying metacarpal bone 34. Thus, the bone plate 40 includes rows 64 and 66 of apertures 63 that are distally spaced from each other, apertures 63 that are laterally spaced from each other, and portions 63a and 63b that are distally spaced from each other a distance less than the rows 64 and 66, and laterally spaced from each other a distance less than the distance between laterally adjacent apertures 63. In the depicted embodiment, the first row 64 of apertures 63 may be spaced from the second row 64 of apertures 63 along the longitudinal direction L. At least one of the distal apertures 63 of the second row 66 can be positioned so as to be aligned with the same metacarpal bone 34 as one of the distal apertures 63 of the first row 64. Thus, at least two of the distal apertures 63 are configured to be aligned with the same metacarpal bone 34 when the proximal portion 46 is disposed over the radius 24 and the distal portion 50 is disposed over the metacarpal bones 34. In the depicted embodiment, two apertures 63 of the first row 64 are longitudinally aligned with two apertures 63 of the second row 66. Accordingly, in operation, one bone anchor can be inserted through the plate body 42 and into the second metacarpal bone 34b, two bone anchors can be inserted through the plate body 42 and into third metacarpal bone 34c, two bone anchors can be inserted through the plate body 42 and into the fourth metacarpal bone 34d, and one bone anchor can be inserted through the plate body 42 and into the fifth metacarpal bone 34e.

Figure 5:
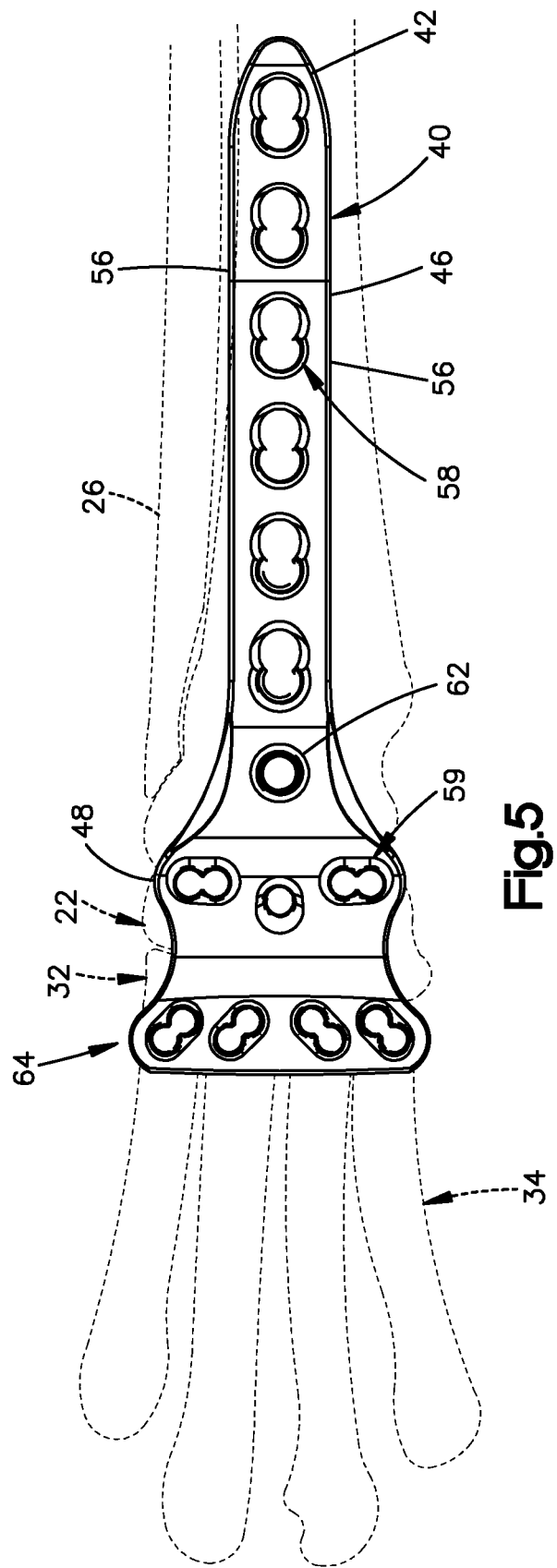
FIG. 5 is a top plan view of a pancarpal arthrodesis bone plate similar to the bone plate illustrated in FIGS. 2A-3, but constructed in accordance with an alternative embodiment.

Referring to FIG. 5, in accordance with an alternative embodiment, the bone plate 40 can be devoid of the second row 66 of apertures 63. While the portions 63a and 63b are open to each other in accordance with the illustrated embodiment, it should be appreciated that the portions 63a and 63b can alternatively be enclosed and spaced from each other. In this embodiment, only one bone anchor can be inserted through the plate body 42 and into each metacarpal bone 34.

With reference to FIG. 2D, the plate body 42 defines a first or proximal end 70 and a second or distal end 72 that is spaced from the first end 70 along the longitudinal direction. Moreover, the plate body 42 defines a first length L1 that extends from the proximal end 70 to the distal end 72 along the longitudinal direction L. The first length L1 may range between about 115 millimeters and about 125 millimeters (mm) For instance, the first length L1 may be about 121.6 mm. The plate body 42 further defines a second length L2 that extends from the proximal end 70 to the center of one of the intermediate apertures 59 along the longitudinal direction. The second length L2 may range between about 84 mm and about 100 mm. For example, the second length may be about 92 mm. The plate body 42 also defines a third length L3 that extends between the center of one of the intermediate apertures 59 to the distal end 72. The third length L3 may range between about 28 mm and about 32 mm. For instance, the third length L3 may be about 29.6 mm. The plate body 42 further defines a first maximum width W1 that extends from one side surface 56 to the opposed side surface 56 at the proximal portion 46. The first width W1 may range between about 9 mm and about 13 mm. For example, the first width W1 may be about 11 mm. The plate body 42 may also define a second maximum width W2 that extends from one side surface 56 to the opposed side surface 56 at the distal portion 50. The second maximum width W2 may range between about 28 mm and about 34 mm. For instance, the second maximum width W2 may be about 32.6 mm. The dimensions described above allow the bone plate 40 to fit over the carpal region 20 of a canine. However, the plate body 42 may have different dimension that allows the bone plate 20 to fit over the carpal region of smaller or larger canines.

Referring to FIG. 6A-C, the illustrated bone plate 40 is substantially similar as the bone plate shown in FIGS. 2A-D. However, in this embodiment, the bone plate 40 includes a third group 78 of distal apertures that are spaced from the first group 74 of distal apertures 63 along the longitudinal direction L. The third group 78 of distal apertures 63 may be disposed between the first group 74 and the second group 76 of distal apertures 63. In the depicted embodiment, the third group 78 may be configured as a third row 68 of apertures 63. To accommodate the third row 68 of apertures 63, the first length L1 of the plate body 42 of this embodiment may be longer than that of the plate body shown in FIG. 2D. The third row 68 of apertures 63 is longitudinally spaced from the first row 64 and the second row 66. Specifically, the third row 68 may be disposed between the first row 64 and the second row 66 of apertures 63. The distal apertures 63 can be spaced from each other along the lateral direction A. In the depicted embodiment, the third row 68 includes two distal apertures 63. However, the third row 68 may include more or fewer apertures 63. The distal apertures 63 of the third row 68 are laterally spaced apart from each other a distance that is larger than the distance between laterally adjacent apertures 63 of the first row 64. Similarly, the distal apertures 63 of the third row 68 are laterally spaced apart from each other a distance that is larger than the distance between laterally adjacent apertures of the second row 66. At least one aperture 63 of the first row 64 can be longitudinally aligned with one aperture 63 of the third row 68. Thus, two bone anchors can be inserted through the plate body 42 and into the same metacarpal bone 34. At least one aperture 63 of the first row 64 can be longitudinally aligned with one aperture 63 of the second row 66. Thus, the distal apertures 63 are configured to be positioned relative to one another such that two apertures 63 are substantially aligned with at least a respective different one of at least four different metacarpal bones 34 when the distal portion 50 is disposed over the metacarpal bones 34 and the proximal portion 46 is disposed over the radius 24.

The addition of the third row 68 of distal apertures 63 allows at least two bone screws to be inserted through the plate body 42 and into each of the metacarpal bone 34 that is fixed to the bone plate 40. For instance, two bone anchor can be inserted through the plate body 42 and into the second metacarpal bone 34b, two bone anchors can be inserted through the plate body 42 and into third metacarpal bone 34c, two bone anchors can be inserted through the plate body 42 and into the fourth metacarpal bone 34d, and two bone anchor can be inserted through the plate body 42 and into the fifth metacarpal bone 34e. The ability to fix two bone anchors to each metacarpal bone 34 that is attached to the bone plate 40 provides better fixation of the bone plate to the metacarpal bones compared to convention pancarpal bone plates.

It should be appreciated that the apertures 58, 59, and 63 can be sized as desired so as to receive bone screws of any size as desired that have a head and a shaft that extends from the head. For instance, in accordance with one embodiment, the proximal apertures 58 can be sized so as to receive bone screws whose shafts have a diameter of approximately 3.5 mm. The intermediate apertures 59 can be sized to receive screws whose shafts have a diameter of approximately 2.7 mm, and the distal apertures 53 can be sized to receive screws whose shafts have a diameter of approximately 2.4 mm. It should be appreciated, however, that the apertures 58, 59, and 63 can be sized to mate with any alternatively sized bone screw as desired.

Thus, a bone fixation kit can include a plurality of bone anchors, such as screws, and at least one bone plate 40 having a plurality of bone anchor apertures that are configured to receive the bone anchors so as to fix the bone plate to the underlying bone. The kit can include more than one plate 40, such as a first bone plate 40 that includes the second row 66 of apertures 63, and a second bone plate 40 that is devoid of the second row 66 of apertures 63. The bone fixation kit can further include a plurality of (e.g., at least two) bone anchors 30 that secure the bone fixation plate 22 to the underlying bone 27 on opposed sides of the bone gap 28. The bone plate 40 can be made from any suitable biocompatible material, such as titanium, including titanium alloys, stainless steel, ceramics, or polymers such as polyetheretherketone (PEEK), cobalt chromium molybdenum (CoCrMo) with a porous plasma-sprayed titanium coating, or any suitable alternative material as desired.

One method of fixing the bone plate 40 to the underlying carpal region 20 includes the step of inserting a bone screw through at least one of the intermediate apertures 59 and into the respective proximal carpal bone 22 so as to fix the intermediate portion 48 to the underlying bone, and subsequently inserting a bone screw through at least one of the distal apertures 63 and into the respective metacarpal bone 34 so as to fix the distal portion 50 to the underlying bone. Accordingly, the bone plate 40 can be first affixed to the carpus at a location distal with respect to the radius 24 so as to fix the proximal carpal bones 22 with respect longitudinal movement relative to the metacarpal bones 34. Next, the method of fixing the bone plate 40 to the underlying carpal region 20 can include the step of inserting a bone screw through at least one of the proximal apertures 58 so as to fix the proximal portion 46 to the underlying radius 24. The method can further include the step of compressing the radius 24 and the proximal carpal bones 22 toward each other prior to fixing the proximal portion 46 with respect to longitudinal movement relative to the underlying radius 24. For instance, the bone screw can be driven through the proximal portion 60a of the combination aperture 60, and the bone plate 40 can be translated proximally, thereby causing the position of the bone screw to translate from the proximal end of the proximal portion 60b to the distal end of the proximal portion 60b. The bone screw can then be tightened against the plate body 42. Additional bone screws can also be inserted into select ones of the proximal apertures 58 as desired so as to prevent relative movement between the radius 24, the proximal carpal bones 22, and the metacarpal bones 34. The bottom of the bone plate 40 can be scalloped so as to provide limited contact with the underlying bone.

As discussed above, the present disclosure also relates to methods of bone fixation. In an embodiment, the method includes one or more of the following steps: (a) placing a bone plate onto a carpal region of a patient, the bone plate including a bone plate body that defines a proximal portion, a distal portion that is spaced from the proximal portion along a longitudinal direction, a plurality of apertures extending through the distal portion, each of the apertures including a first portion and a second portion that is spaced from the first portion and open to the first portion, each of the first and second portions configured and sized to individually receive a bone anchor; (b) positioning the bone plate body on the carpal region such that the proximal portion overlays at least a portion of a radius of the carpal region and the distal portion overlays at least four metacarpal bones; (c) identifying a select one of the first and second portions of at least one of the apertures to receive a bone anchor; and (d) inserting the bone anchor through the identified select one of the first and second portions of the at least one of the apertures so as to attach the distal portion to at least one of the metacarpal bones. The placing step may include aligning at least one of the apertures with each of the four metacarpal bones. The placing step may include aligning at least two of the apertures with each of the four metacarpal bones. The apertures may be distal apertures, and the bone plate may further define proximal apertures at the proximal region. The bone screw may be a distal bone screw, and the method may further include inserting a proximal bone screw through at least one of the proximal apertures and into the radius so as to couple to bone plate to the radius.

The embodiments described in connection with the illustrated embodiments have been presented by way of illustration, and the present invention is therefore not intended to be limited to the disclosed embodiments. For instance, it is envisioned that the arthrodesis bone plate 40 can be affixed to the tarsal region of a quadruped substantially in the manner described above with respect to the carpal region. Furthermore, the structure and features of each the embodiments described above can be applied to the other embodiments described herein, unless otherwise indicated. Accordingly, those skilled in the art will realize that the invention is intended to encompass all modifications and alternative arrangements included within the spirit and scope of the invention, for instance as set forth by the appended claims.

The invention claimed is:

1. An arthrodesis bone plate configured to be attached to a carpal region of a patient, the arthrodesis bone plate comprising:

a bone plate body that is elongate along a longitudinal axis that extends in a longitudinal direction, the bone plate body defining a bone-facing inner surface and an opposed outer surface that is spaced from the inner surface along a transverse direction that is perpendicular to the longitudinal direction, the bone plate body including a proximal portion and a distal portion that is spaced from the proximal portion in a distal direction along the longitudinal direction that is substantially perpendicular to the transverse direction, the proximal portion configured to be positioned over a radius of the carpal region, the distal portion configured to be positioned over metacarpal bones of the carpal region;

wherein 1) the bone plate body defines a plurality of apertures that extend from the outer surface to the inner surface at the distal portion, a group of the plurality of apertures including individual apertures that are spaced from one another along a lateral direction that is substantially perpendicular to the longitudinal and transverse directions, such that each individual aperture of the group is substantially aligned with at least a respective different one of at least four different metacarpal bones when the distal portion is positioned over the metacarpal bones and the proximal portion is positioned over the radius; 2) each of the individual apertures of the group includes a first portion and a second portion that is open to the first portion along a respective aperture axis, and each of the apertures is elongate along the respective aperture axis, the first portion offset with respect to the second portion, each of the first and second portions of each individual aperture of the group configured to singly receive a bone anchor along respective first and second central axes that intersect the aperture axis so as to attach the distal portion of the bone plate body to the respective four different metacarpal bones, such that at least one of the first and second portions of an individual aperture of the group is defined by a partially threaded surface; and 3) the individual apertures of the group of apertures include first and second apertures positioned on opposed sides of the longitudinal axis, such that the aperture axis of each of the first and second apertures extends away from the longitudinal axis as it extends the in distal direction.

2. The arthrodesis bone plate of claim 1, wherein the first portion is offset with respect to the second portion in both the longitudinal direction and the lateral direction.

3. The arthrodesis bone plate of claim 1, wherein the plurality of apertures is a plurality of distal apertures, and the bone plate further comprises a plurality of proximal apertures that extend from the outer surface to the inner surface at the proximal portion, each proximal aperture is configured to receive a bone anchor so as to attach the proximal portion of the bone plate body to the radius.

4. The arthrodesis bone plate of claim 3, wherein the proximal apertures are spaced from one another along the longitudinal direction.

5. The arthrodesis bone plate of claim 3, wherein the bone plate body further comprises an intermediate portion that is disposed between and longitudinally spaced from the proximal and distal portions, and the intermediate portion is configured to be positioned over a radial carpal bone and an ulnar carpal bone of the carpal region when the proximal portion is positioned over the radius and the distal portion is positioned over the metacarpal bones.

6. The arthrodesis bone plate of claim 5, wherein the intermediate portion comprising a plurality of intermediate apertures, each of the intermediate apertures configured to receive a bone anchor so as to attach the intermediate portion of the bone plate to the radial carpal bone and the ulnar carpal bone.

7. The arthrodesis bone plate of claim 6, wherein the intermediate apertures are spaced from each other along the lateral direction such that at least one intermediate aperture is aligned with the radial carpal bone and another intermediate aperture is aligned with the ulnar carpal bone when the bone plate body is positioned over the carpal region.

8. The arthrodesis bone plate of claim 1, wherein the partially threaded surface includes a first threaded surface that partially defines the first portion of at least one of the apertures, a second threaded surface that partially defines the second portion of at least one of the apertures, and a substantially flat surface that is positioned between the first and second threaded surfaces so as to separate the first portion from the second portion.

9. The arthrodesis bone plate of claim 1, wherein the group of the plurality of apertures is a first row that extends along the lateral direction.

10. The arthrodesis bone plate of claim 1, wherein the group is a first group, and the plurality of apertures includes a second group that is spaced from the first group along the longitudinal direction.

11. The arthrodesis bone plate of claim 10, wherein at least two of the apertures of the plurality of apertures are configured to be aligned with the same metacarpal bone when the proximal portion is positioned over the radius and the distal portion is positioned over the metacarpal bones.

12. The arthrodesis bone plate of claim 10, wherein the plurality of apertures includes a third group of apertures that is spaced from the first and second groups along the longitudinal direction, and the third group of apertures is disposed between the first group and the second group of apertures.

13. The arthrodesis bone plate of claim 1, wherein the proximal portion is offset with respect to the distal portion along the transverse direction.

14. The arthrodesis bone plate of claim 1, wherein the proximal portion is offset with respect to an intermediate portion along the transverse direction.

15. The arthrodesis bone plate of claim 1, wherein the bone plate body defines a threaded surface and an unthreaded surface that cooperate to define at least one of the plurality of apertures, and the unthreaded surface is spaced from the threaded surface along the transverse direction.

16. The arthrodesis bone plate of claim 1, wherein the bone plate body further defines a respective pair of necks that connect between the first and second portions of each of the individual apertures, each of the necks defining at least one substantially flat unthreaded surface that is substantially planar along both the transverse direction and a first direction that is substantially parallel to the aperture axis.

17. The arthrodesis bone plate of claim 16, wherein the aperture axis of each individual aperture extends equidistantly between the respective necks.

18. The arthrodesis bone plate of claim 1, wherein the aperture axis of each individual aperture extends over respective geometric centers of the respective first and second portions,
the bone plate body further defining a respective neck connected between the first and second portions of each of the individual apertures, the neck defining at least one substantially flat unthreaded surface that is substantially planar along both the transverse direction and a first direction that is parallel to the aperture axis.

19. An arthrodesis bone plate configured to be attached to a carpal region of a patient, the arthrodesis bone plate comprising:
a bone plate body that is elongate along a longitudinal direction, the bone plate body defining a bone-facing inner surface and an opposed outer surface that is spaced from the inner surface along a transverse direction, the bone plate body including a proximal portion and a distal portion that is spaced from the proximal portion along the longitudinal direction that is substantially perpendicular to the transverse direction, the proximal portion configured to be positioned over a radius of the carpal region, the distal portion configured to be positioned over metacarpal bones of the carpal region;
wherein the bone plate body defines a plurality of apertures that 1) are each elongate along a respective first direction and, 2) extend from the outer surface to the inner surface at the distal portion, the plurality of apertures including a group of apertures, the apertures of the group of the plurality of the apertures being spaced from one another along a lateral direction that is substantially perpendicular to the longitudinal and transverse directions, such that each of the apertures of the group is substantially aligned with at least a respective different one of at least four different metacarpal bones when the distal portion is positioned over the metacarpal bones and the proximal portion is positioned over the radius, and each of the apertures of the group includes a first portion and a second portion that is both open to the first portion and offset with respect to the first portion along the respective first direction, each of the respective first directions being non-parallel to both the longitudinal direction and the lateral direction, such that each of the apertures is elongate along the respective first direction, each of the first and second portions of each aperture of the group configured to singly receive a bone anchor so as to attach the distal portion of the bone plate body to the respective four different metacarpal bones, the bone plate body further defining a neck that is connected between the first and second portions of each aperture, the neck defining at least one substantially flat surface that is unthreaded along the transverse direction from the inner surface to the outer surface, and is substantially planar along both the respective first direction and the transverse direction.

20. The arthrodesis bone plate of claim 19, wherein the substantially flat unthreaded surface is a first substantially flat unthreaded surface, and the bone plate body further defines a second substantially flat unthreaded surface that is positioned between the first and second portions, the first substantially flat unthreaded surface is spaced from the second substantially flat unthreaded surface along a second direction that is substantially perpendicular to the first direction.

21. The arthrodesis bone plate of claim 19, wherein at least two apertures in the plurality of apertures are configured to be substantially aligned with a single metacarpal bone of the metacarpal bones when the bone plate body is positioned over the carpal region.

22. The arthrodesis bone plate of claim 19, wherein a first and second of the respective first directions are parallel to one another.

23. The arthrodesis bone plate of claim 19, wherein a first and second of the respective first directions are non-parallel to one another.

* * * * *